United States Patent [19]
Mendelson et al.

[11] Patent Number: 5,866,427
[45] Date of Patent: Feb. 2, 1999

[54] IN VITRO PROTON MRS DETECTION OF FREQUENCY AND AMOUNT OF ALCOHOL SELF-ADMINISTRATION

[75] Inventors: Jack H. Mendelson; Nancy K. Mello, both of Rockport; Tak-Ming Chiu, Belmont, all of Mass.

[73] Assignee: The McLean Hospital Corporation, Belmont, Mass.

[21] Appl. No.: 873,896

[22] Filed: Jun. 13, 1997

Related U.S. Application Data

[60] Provisional application No. 60/019,896, Jun. 13, 1996.

[51] Int. Cl.$^6$ .......................... G01N 33/98; G01N 33/48; G01N 33/49
[52] U.S. Cl. ........................... 436/63; 436/131; 436/132; 436/173
[58] Field of Search ........................... 436/63, 131, 132, 436/173; 600/410; 324/300

[56] References Cited

PUBLICATIONS

Besson, J.A.O., et al., "$^1$H–NMR Relaxation Times and Water Content of Red Blood Cells from Chronic Alcoholic Patients During Withdrawl," *Mag. Res. Imag.* 7:289–291 (1989).

Besson, J.A.O., et al., "The Effects of Progressive Abstinence from Alcohol on Red Blood Cell Proton NMR Relaxation Times and Water Content," *Alcoholism: Clinical and Experimental Research* 15(2):181–183 (1991).

Bock, J.L., "Analysis of Serum by High–Field Proton Nuclear Magnetic Resonance," *Clin. Chem.* 28(9):1873–1877 (1982).

Brown, F.F., et al., "Human Erythrocyte Metabolism Studies by $^1$H Spin Echo NMR," *FEBS Lett.* 82(1):12–16 (1977).

Chiou, J.–S., et al., "Anesthesia Cutoff Phenomenon: Interfacial Hydrogen Bonding," *Science* 248:583–585 (1990).

Chiou, J.–S., et al., "Interfacial Dehydration by Alcohols: Hydrogen Bonding of Alcohols to Phospholipids," *Alcohol* 8:143–150 (1991).

Chiu, T.–M., et al., "In Vivo Proton Magnetic Resonance Spectroscopy Detection of Human Alcohol Tolerance," *Mag. Reson. Med.* 32:511–516 (1994).

Conte, A., et al., "Effect of L–Propionyl Carnitine on Some Properties of Erythrocytes and Leukocyctes of Alcohol Abusers," *Int. J. Tiss. Reac.* XVII(1):21–31 (Jan. 1995).

Davin, A., et al., "Rapid Evaluation of Ethanol Content and Metabolism in Human Plasma Using Quantitative Proton Magnetic Resonance Spectroscopy," *Alcohol and Alcoholism* 29(5):479–482 (1994).

Gentry, R.T., et al., "Serial Determination of Plasma Ethanol Concentrations in Mice," *Physiology and Behavior* 31:529–532 (1983).

Goldstein, D.B., "Ethanol–Induced Adaptation in Biological Membranes," *Ann. N. Y. Acad. Sci.* 492:103–111 (1987).

(List continued on next page.)

*Primary Examiner*—Arlen Soderquist
*Attorney, Agent, or Firm*—Bterne, Kessler, Goldstein & Fox P.L.L.C.

[57] ABSTRACT

In the method of the invention, in vitro proton MRS is employed to determine the measurable ethanol concentrations in ethanol-treated erythrocyte samples of occasional and heavy drinkers. An erythrocyte to plasma ethanol concentration ratio is determined based upon the MRS measured erythrocyte concentration. Erythrocyte to plasma ethanol concentration ratios are significantly greater for heavy drinkers (a subset of alcohol tolerant individuals) as compared to the ratios calculated for occasional drinkers (non-tolerant individuals) when erythrocyte ethanol concentration is determined by MRS. Thus, the method of the present invention discriminates between alcohol tolerant individuals and alcohol non-tolerant individuals based upon the magnitude of the erythrocyte to plasma ethanol concentration ratio obtained according to the methods disclosed herein.

16 Claims, 7 Drawing Sheets

PUBLICATIONS

Irving, M.G., et al., "Application of the Reverse DEPT Polarization–Transfer Pulse Sequence to Monitor In Vitro and In Vivo Metabolism of $^{13}$C–Ethanol by $^1$H–NMR Spectroscopy," *Int. J. Biochem.* 17(4):471–478 (1985).

Jones, A.J., and Kuchel, P.W., "Measurement of Choline Concentration and Transport in Human Erythrocytes by $^1$H NMR: Comparison of Normal Blood and That from Lithium–Treated Psychiatric Patients," *Clin. Chim. Acta* 104:77–85 (1980).

Kaufman, M.J., et al., "In Vivo Proton Magnetic Resonance Spectroscopy of Alcohol in Rhesus Monkey Brain," *Mag. Reson. Imag.* 12(8):1245–1253 (1994).

Koob, G.F., and Bloom, F.E., "Cellular and Molecular Mechanisms of Drug Dependence," *Science* 242:715–723 (1988).

Kriat, M., et al., "Quantitation of Metabolites in Human Blood Serum by Proton Magnetic Resonance Spectroscopy. A Comparative Study of the Use of Formate and TSP as Concentration Standards," *NMR in Biomedicine* 5:179–184 (1992).

Mendelson, J.H., and Mello, N.K., "Biologic Concomitants of Alcoholism," *N. Engl. J. Med.* 301(17):912–921 (1979).

Mendelson, J.H., et al., "In Vivo Proton Magnetic Resonance Spectroscopy of Alcohol in Human Brain," *Alcohol* 7:443–447 (1990).

Pappas, A.A., et al., "High–Resolution Proton Nuclear Magnetic Resonance Spectroscopy in the Detection and Quantitation of Ethanol in Human Serum," *J. Anal. Toxicol.* 17:230–232 (1993).

Rabenstein, D.L., "$^1$H NMR methods for the noninvasive study of metabolism and other processes involving small molecules in intact erythrocytes," *J. Biochem. Biophys. Meth.* 9:277–306 (1984).

Spielman, D.M., et al., "Magnetic Resonance Spectroscopic Imaging of Ethanol in the Human Brain: A Feasibility Study," *Alcoholism: Clinical and Experimental Research* 17(5):1072–1077 (1993).

Tsai, Y.–S., et al., "Fourier Transform Infrared Studies on Phospholipid Hydration: Phosphate–Oriented Hydrogen Bonding and Its Attenuation by Volatile Anesthetics," *Mol. Pharmacol.* 31:623–630 (1987).

IN VITRO PROTON MRS DETECTION OF FREQUENCY AND AMOUNT OF ALCOHOL SELF-ADMINISTRATION

This application claims priority under 35 U.S.C. §119(e) to U.S. provisional application Ser. No. 60/019,896, filed Jun. 13, 1996.

BACKGROUND OF THE INVENTION

1. Field of the Invention

The present invention generally relates to clinical in vitro proton ($^1$H) magnetic resonance spectroscopy (MRS). More specifically, the present invention is directed to the application of in vitro $^1$H magnetic resonance spectroscopy in a method to detect the past history of an individual's alcohol use (frequency and amount of consumption).

2. Related Art

Acquired alcohol tolerance in humans is proportional to the amount of ethanol consumed and the frequency of drinking (Mendelson & Mello, *N. Engl. J. Med.* 301:912–821 (1979); Kalant, H., in "Biology of Alcoholism", Kissin & Begleiter, eds., Plenum Press, New York, N.Y. (1971), pp. 1–26). The degree of chronic ethanol tolerance often is correlated with the severity of ethanol dependence, but alcohol tolerance may also develop in occasional drinkers who do not abuse alcohol and are not alcohol dependent.

The specific mechanisms which subserve the development of ethanol tolerance are unknown. A number of interrelated processes, including ethanol-induced changes in plasma membranes and membrane-bound water, probably are involved intolerance (Goldstein, D. B., *Ann. N.Y. Acad. Sci.* 492: 103–111 (1987); Hunt, W. A., "Alcohol and Biological Membranes," Guilford Press, New York N.Y. (1985), p. 3; Hoek & Taraschi, *Trends Biochem. Sci.* 13:269–274 (1988); Koob & Bloom, *Science* 242:715–723 (1988)). Binding of ethanol to hydrophilic phosphates of phospholipid head groups located on the surface of cell membranes may also vary as a function of ethanol tolerance as a consequence of the effects of ethanol on membrane phospholipid structures (Chin & Goldstein, *Science* 196:684–685 (1977); Rottenberg et al., *Science* 213:583–585 (1981); Taraschi et al., *Proc. Natl. Acad. Sci. USA* 83:3669–3673 (1986); Taraschi et al., *Proc. Natl. Acad. Sci. USA* 83:9398–9402 (1986); Waring et al., *Proc. Natl. Acad. Sci. USA* 78:2528–2586 1981); Tsai et al., *Mol. Pharmacol.* 31:623–630 (1987); Chiou et al., *Science* 248:583–585 (1990); Chiou et al., *Alcohol* 8:143–150 (1991)).

Proton MRS has been employed to qualitatively identify organic compounds, including ethanol, in human serum (Boch, J. L., "Analysis of serum by high-yield proton nuclear magnetic resonance," *Clin. Chem.* 28:1873–1877 (1982)). Boch suggests that proton MRS may also be used quantitatively to determine the concentration of some organic chemicals in human plasma by determining the areas under relevant peaks on the MRS chemical shift versus peak height spectrum.

Proton MRS has also been employed to study the effects of chronic alcohol on the water content of red blood cells. Besson, J. A. O. et al., "$^1$H-NMR Relaxation Times and Water Content of Red Blood Cells for Chronic Alcoholic Patients during Withdrawal," *Magnetic Resonance Imaging* 7:289–291 (1989) discloses that changes in $T_1$ and $T_2$ relaxation time occur in red blood cells in patients with chronic alcoholism. The reported results indicated that the $T_1$ values for red blood cells of chronic alcoholics were significantly increased compared with controls. The $T_2$ values for red blood cells of chronic alcoholics were also significantly increased compared with controls. The authors hypothesized that altered $T_1$ reflects some disruption in the free-bound state of water, possibly secondary to membrane changes.

Besson, J. A. O. et al., "The Effects of Progressive Abstinence from Alcohol on Red Blood Cell Proton NMR Relaxation Times and Water Content," *Alcoholism: Clinical and Experimental Research* 15:181–183 (1991) discloses that red blood cell proton relaxation times $T_1$ and $T_2$ measured in abstinent chronic alcoholic patients, were elevated in the early stages of abstinence and declined to control values after eight weeks of abstinence. The authors also reported that $T_1$ levels are increased in brain gray and white matter of chronic alcoholic individuals, with the $T_1$ level falling toward control levels after 3 months.

Chiu, P. et al., "In vivo proton magnetic resonance spectroscopy detection of human alcohol tolerance," *Magnetic Resonance in Medicine* 32:511–515 (1994) discloses that brain-blood ethanol concentration ratios for heavy drinkers were significantly greater than brain-blood ethanol concentration ratios for occasional drinkers when brain ethanol concentration is measured by MRS. The reference suggests that in vivo brain MRS can be employed to discriminate between individuals who are alcohol tolerant (frequently consume alcohol) and alcohol non-tolerant (occasionally consume alcohol) individuals.

Kaufman, M. J. et al., "In vivo Proton Magnetic Resonance Spectroscopy of Alcohol and Rhesus Monkey Brain," *Magnetic Resonance Imaging* 12:1245–1253 (1994) describes measurement of brain alcohol levels in Rhesus monkeys by in vivo proton MRS following acute alcohol administration. The reference suggests that MRS-visibility of brain alcohol is related to the history of alcohol exposure and degree of alcohol tolerance of the non-human primate subject.

Harasymiv, U.S. Pat. No. 5,126,271 discloses a method for determining the consumption rate of alcohol by a human subject by developing a serum panel that includes at least twelve constituents. Two of the constituents are HDL and magnesium.

A need currently exists in the art for a routine screening method for objectively discriminating between individuals who are alcohol tolerant individuals (frequently consume alcohol) and alcohol non-tolerant (occasional drinkers) individuals. The in vivo brain MRS method suggested by Chiu et al. has the benefit of being non-invasive. However, many hospitals are not equipped with the necessary facilities to perform in vivo brain MRS imaging. The in vivo method also requires administration of ethanol to the subject. It would be preferable to avoid administering ethanol to a subject as part of a medical screening test.

SUMMARY OF THE INVENTION

The present invention relates to an in vitro method of detecting the frequency and amount of alcohol consumption by a subject. The method employs proton MRS to analyze red blood cells (also referred to herein as erythrocytes or RBCs) isolated from a subject's blood sample. The method discriminates between alcohol tolerant individuals, for example heavy drinkers, and alcohol non-tolerant individuals, such as occasional drinkers, without having to administer ethanol to them.

In the method of the invention, in vitro proton MRS is employed to determine the measurable ethanol concentrations in ethanol-treated erythrocyte samples of occasional and heavy drinkers. An erythrocyte to plasma ethanol concentration ratio is obtained based upon the MRS-measured erythrocyte concentration. Erythrocyte to plasma ethanol concentration ratios are significantly greater for heavy drinkers (a subset of alcohol tolerant individuals) as compared to the ratios calculated for occasional drinkers (a subset of non-tolerant individuals) when erythrocyte ethanol concentration is determined by MRS. Thus, the method of the present invention discriminates between alcohol tolerant individuals and alcohol non-tolerant individuals based upon the magnitude of the erythrocyte to plasma ethanol concentration ratio obtained according to the methods disclosed herein.

The method of the invention is useful for monitoring individuals recovering from alcoholism. In as much as ethanol tolerance covaries with the severity of dependence, the method of the invention is expected to facilitate the understanding of alcohol tolerance and treatment of alcoholism.

It is accordingly one object of the present invention to provide a method of determining the frequency and amount of alcohol self-administration employing in vitro proton magnetic resonance spectroscopy.

Another object of the present invention is to provide a method of monitoring the adequacy or duration of alcohol abstinence in recovering alcoholics.

A further object of the present invention is to provide a method of discriminating occasional alcohol consumption from moderate or heavy alcohol consumption and alcohol abuse.

A still further object of the present invention is to provide a method of determining whether a subject is alcohol tolerant or alcohol non-tolerant.

The in vitro method disclosed herein is expected to be broadly applicable since blood samples can be easily obtained from a subject and thereafter analyzed at a time and location that are convenient to the clinician.

BRIEF DESCRIPTION OF THE FIGURES

FIG. 1B shows an ethanol triplet at 1.26 ppm and a formate resonance at approximately 8.55 ppm.

FIG. 2B shows an ethanol triplet at 1.26 ppm and a formate resonance at approximately 8.55 ppm.

DETAILED DESCRIPTION OF THE PREFERRED EMBODIMENTS

The present invention provides a method for determining the past history of frequency and amount of alcohol self-administration by a subject. The method relies upon the discovery that proton MRS-detected ethanol concentration in erythrocytes ($[ETOH]_{RBC/MRS}$) is parametrically related to MRS-detected ethanol concentration in the brain. Thus, erythrocyte/plasma ethanol ratios for alcohol tolerant individuals, will be significantly greater than the erythrocyte plasma ethanol ratios for alcohol non-tolerant individuals, under identical analytical conditions, that is, when the erythrocyte samples of each are exposed to equal amounts of ethanol.

Figure 3:
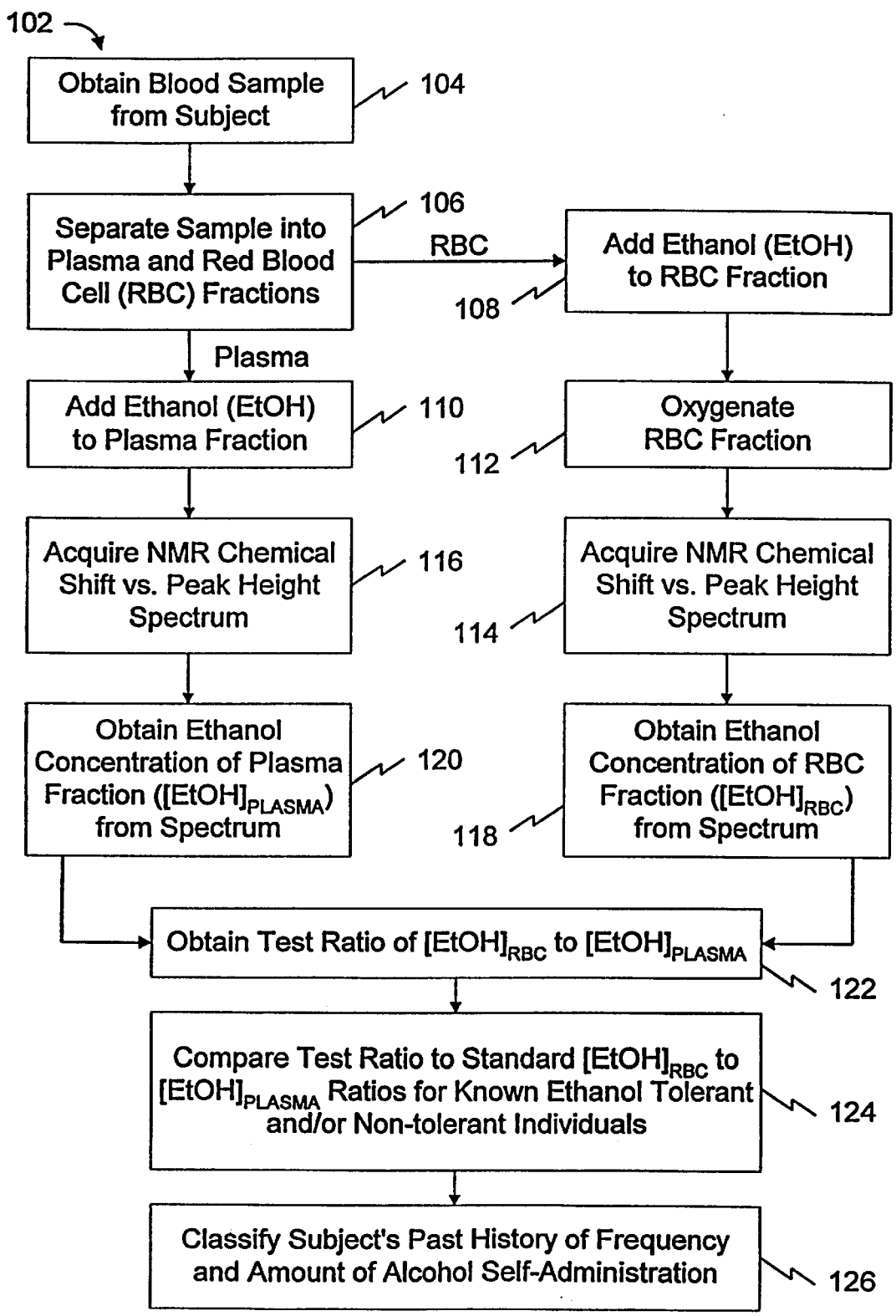
FIG. 3 is a flowchart depicting the steps of a preferred embodiment of the present invention.

As shown in the flowchart 102, in FIG. 3, this embodiment of the method comprises the following steps:

(a) obtaining a blood sample from a subject, step 104;

(b) separating the sample into a plasma fraction and an erythrocyte (RBC) fraction, step 106;

(c) adding an equivalent amount of an ethanol solution to each of said fractions to form an ethanol/erythrocyte solution and an ethanol/plasma solution, step 108 and step 110;

(d) bubbling oxygen through the ethanol/erythrocyte solution to form an oxygenated ethanol/erythrocyte solution, step 112;

(e) acquiring one or more proton magnetic resonance spectra of the oxygenated ethanol/erythrocyte solution, step 114;

(f) obtaining the MRS-measured erythrocyte ethanol concentration ($[ETOH]_{RBC/MRS}$) from said one or more spectra, step 118;

(g) obtaining the ethanol concentration of the ethanol/plasma solution ($[ETOH]_{PLASMA}$) step 116 and step 120;

(h) calculating the ratio of MRS-measured erythrocyte ethanol concentration to plasma ethanol concentration to obtain a test ratio ($\{[ETOH]_{RBC/MRS}:[ETOH]_{PLASMA}\}_{TEST}$), step 122; and (i) comparing said test ratio to one or more known standard values for control subjects having a known past history of frequency and amount of alcohol self-administration, step 124;

whereby the subject's past history of frequency and amount of alcohol self-administration is classified according to the test ratio's relationship to said standard value, step 126.

The relationship of the test ratio to the standard value is dependent upon the standard values that are chosen. For instance, the test value for a subject that self-administers will be elevated compared to standard values obtained by analysis of blood samples taken from individuals who do not self-administer alcohol.

It is contemplated that the method of this aspect of the present invention will find broad application in the transportation industry or other industries where public safety maybe jeopardized by individuals operating machines or equipment under the influence of alcohol. Potential and current employees can be objectively tested to determine, or to aid in determining, the history of alcohol consumption of these individuals over the past six months to a year. The method of the present invention will effectively discriminate between individuals who consumed two to four drinks per week and individuals who regularly consumed ten to twenty drinks per week. Thus, the method of the present invention can provide valuable information to employers and public safety officers regarding the frequency and amount of alcohol self-administration of an individual entrusted to safely operate a mode of transportation, such as a train or ship, or who is entrusted to operate a machine or device that is potentially, hazardous.

An second aspect of the present invention lies in monitoring the adequacy or duration of alcohol abstinence in a test subject comprising the following steps:

(a) obtain a blood sample from a test subject;

(b) separate the sample into an erythrocyte fraction and a plasma fraction;

(c) incubate each fraction with a fixed amount of ethanol;

(d) oxygenate the ethanol-treated erythrocyte fraction;

(e) determine ethanol concentration of the oxygenated, ethanol-treated erythrocyte fraction by MRS ($[EtOH]_{RBC/MRS}$);

(f) determine ethanol concentration of the ethanol-treated plasma fraction ($[EtOH]_{PLASMA}$);

(g) obtain a test ratio of $[EtOH]_{RBC/MRS}:[EtOH]_{PLASMA}$; and (h) compare the test ratio to a known standard value for one or more control subjects having a known past history of alcohol abstinence, whereby the test subject's abstinence can be determined by a progressively decreasing test ratio that approaches the standard value.

It is contemplated that a subject's abstinence will be monitored by repeating the method steps over a time interval spanning weeks or months. Over time the test ratio for an abstinent subject recovering from alcoholism should approach, and eventually reach, a value that is equivalent to the standard value obtained from a known abstinent or alcohol non-tolerant individual. This aspect of the present invention has particular utility in monitoring subjects that are attempting recovery from alcoholism.

A third aspect of the present invention is a method for determining whether a subject is alcohol tolerant or non-tolerant comprising the following steps:

(a) obtain a blood sample from a test subject;

(b) separate the sample into an erythrocyte fraction and a plasma fraction;

(c) incubate each fraction with a fixed amount of ethanol;

(d) oxygenate the ethanol-treated erythrocyte fraction;

(e) determine ethanol concentration of the oxygenated, ethanol-treated erythrocyte fraction by MRS ($[EtOH]_{RBC/MRS}$);

(f) determine ethanol concentration of the ethanol-treated plasma fraction ($[EtOH]_{PLASMA}$);

(g) obtain a test ratio of $[EtOH]_{RBC/MRS}:[EtOH]_{PLASMA}$; and (h) compare the test ratio to a known standard value obtained from one or more control subjects that are known to be either alcohol tolerant or alcohol non-tolerant, whereby a test ratio which is elevated compared to said standard value obtained from one or more alcohol non-tolerant control subjects is indicative that the subject is alcohol tolerant.

Tolerance, as used in herein, refers to progressive loss of sensitivity of an organism to a given dose of a drug with repeated use. Alcohol tolerance refers to general behavioral tolerance as well as physiological tolerance that occurs in human subjects as the result of repeated ingestion of alcohol and/or the administration of other chemical agents that contribute to tolerance of alcohol.

Plasma ethanol concentration, also referred to herein as $[ETOH]_{PLASMA}$, can be determined by methods generally known in the art, for instance, by gas chromatography, or can also be determined by MRS. Preferably, plasma ethanol concentration is determined by in vitro proton MRS in a manner equivalent to the determination of erythrocyte concentration by MRS.

The phrase "past history of frequency and amount of alcohol self-admintstration," as used herein, refers to the average number of drinks, as defined herein, per week that a subject has consumed over a period of up to the preceding two months. For example, heavy drinkers are individuals that regularly consume about 10 to about 20 drinks per week. Occasional drinkers are individuals who consume about 2 to about 4 drinks per week. Abstinent individuals avoid self-administering alcohol altogether.

The term "drink" as employed herein is defined as 1 ounce of distilled spirits containing about 43% ethanol 6 ounces of wine containing 12–14% ethanol or 12 ounces of beer containing about 6% ethanol.

The term "standard value(s)" as employed herein refers to one or more erythrocyte ethanol concentration: plasma ethanol concentration ratios that have been determined for control subjects who have a known past history of frequency and amount of alcohol self-administration, who are known to be alcohol tolerant or non-tolerant, or who are known to have a past history of alcohol abstinence. A standard value can be a single value determined for one or more subjects known to self-administer alcohol at a specific amount and frequency. The range of values for the erythrocyte ethanol concentration: plasma ethanol concentration ratio are expected to range from about 0.2 to about 0.3 for alcohol non-tolerant subjects and from about 0.4 to about 0.8 for alcohol tolerant subjects. It is further contemplated that a standard curve can be constructed with ratios obtained from a group of subjects that possess a range of frequency and amount of alcohol self-administration, such that the curve represents a series of standard values to which a test ratio can be easily compared.

For the method of determining the frequency and amount of alcohol self-administration useful standard values will include erythrocyte ethanol concentration to plasma ethanol concentration ratios (control ratios) determined for a number of control subjects that vary in their frequency and amount of alcohol self-administration. A standard curve can be constructed employing ratios that have been obtained for a number of individuals whose past history of alcohol self-administration has been reliably determined employing conventional assessment protocols and whose past history of alcohol use spans the spectrum of abstinence to chronic abuse of alcohol. The frequency and amount of alcohol self-administration for a test subject can be determined by comparing the test ratio to the standard curve. Alternatively, for each of the methods of the present invention a test ratio can be compared to a control ratio obtained for a control subject that is known to be alcohol tolerant or alcohol non-tolerant. Test ratios that are significantly greater than control ratios obtained from non-tolerant individuals indicate moderate to heavy alcohol self-admnstration within the past six months. Test ratios that are significantly less than ratios obtained for control ratios obtained from alcohol tolerant individuals indicate abstinence or only occasional alcohol self-administration within the past two months.

Figure 5:
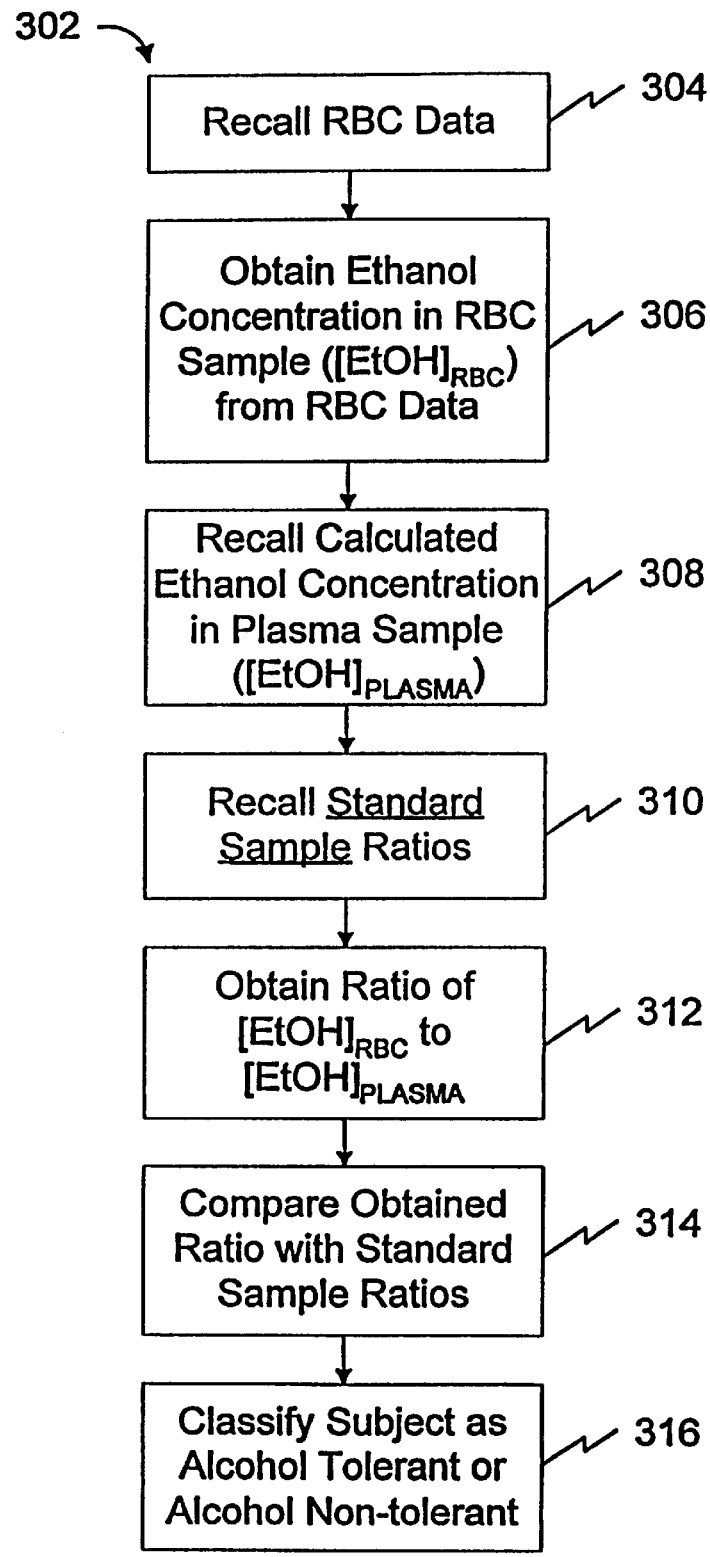
FIG. 5 is a flowchart depicting exemplary data analysis steps that are involved in classifying a subject's recent history of frequency and amount of alcohol self-administration.

It is further contemplated that previously determined control values and control ratios can be stored on a suitable memory device that can be accessed by a central processing unit that is integrally related to the MRS spectrometer or is separate from the spectrometer. The calculations required in determining the ratios can be performed without the aid of a computer, but are preferably carried out on a central processing unit that is integrally related to the MRS spectrometer or is linked to the MRS spectrometer such that data can be communicated to the central processing unit. Flowchart 302 in FIG. 5 depicts the steps that may be accomplished with the aid of a computing device such as a central processing unit. The chemical shift versus peak height spectrum (RBC data) is recalled from memory, step 304. The ethanol concentration in the erythrocyte fraction is determined by obtaining the peak areas of the ethanol peak and the formate concentration standard peak step 306. The ethanol concentration of the plasma fraction is recalled, step 308. This concentration can be determined by methods analogous to those used for the erythrocyte fraction, or alternate methods, such as gas chromatography, can be employed. Previously determined $[EtOH]_{RBC/MRS}$:$[EtOH]_{PLASMA}$ ratios for standard samples are recalled, step 310. The test ratio is obtained, step 312, from the data recalled in steps 306 and 308. The test ratio is then compared, step 314, to one or more standard ratios recalled in step 310 and the test subject is classified as alcohol tolerant or alcohol non-tolerant based upon this comparison, step 316.

Modifications within the skill of the art that are equivalent to the claimed methods include contacting the blood sample of a subject with ethanol before the sample is separated in to plasma and erythrocyte fractions. Although the magnitude of the measurable ethanol concentrations may vary compared to samples that are separated prior to mixing with ethanol, the resultant ratios obtained for tolerant individuals are expected to remain significantly larger than the ratios obtained for non-tolerant individuals.

The blood samples that are collected are preferably venous samples due to the ease of collecting and handling venous samples. An anticoagulant, such as ethylenediamine tetraacetic acid (EDTA) or ammonium heparin, is preferably added to the samples. The samples are conveniently separated into red blood cells and plasma by centrifugation of the blood sample. For example, a blood sample may be spun at 1500 rpm for ten minutes using a Damon/IEC #HN-S clinical table top centrifuge (Newton, Mass.). The plasma can then be separated using serum separators.

Preferably, ethanol is added to the red blood cell fraction and the plasma fraction in a saline solution. The final ethanol concentration is in the range of about 75 to about 125 mg/dL, preferably about 100 mg/dL (21.7 mM). After the erythrocyte fraction is oxygenated to ensure that hemoglobin is in the diamagnetic oxygenated form, the fraction is placed in an NMR sample tube. Sodium formate is preferably employed as a concentration standard, as has been done previously in NMR studies of human blood plasma (Davin et al., *Alcohol Alcoholism.* 29:479–483 (1994) and serum (Kriat, M., *NMR in Biomedcine* 5:179–184 (1992). Sodium formate has a single resonance at ~8.5 ppm, and is free from interference from other resonances. Excellent linear correlation (r=0.989) was found between sodium formate concentration and its corresponding peak integral over a 20-fold concentration range (12 mM–250 mM). Other chemicals that do not interfere with detection of the ethanol peaks may also be included. A reference for chemical shift, for example, tetradeutero-3-trimethylsilylpropionate (TSP) may be added.

Formation of NMR spectra is not instantaneous. As is well known, a number of steps are required including application of radio frequency energy pulses to the sample, creating gradients in the magnetic field, and detecting radio frequency signals emitted by the sample. These steps are repeated many times for each imaging cycle. Thereafter, a spectrum of chemical shift versus peak height is formed from the accumulated data. From this spectrum, one can conveniently determine the concentration of constituents, by determining the area under the peak of the sodium formate concentration standard and the area under the ethanol peak and extrapolating the ethanol concentration.

Figure 4:
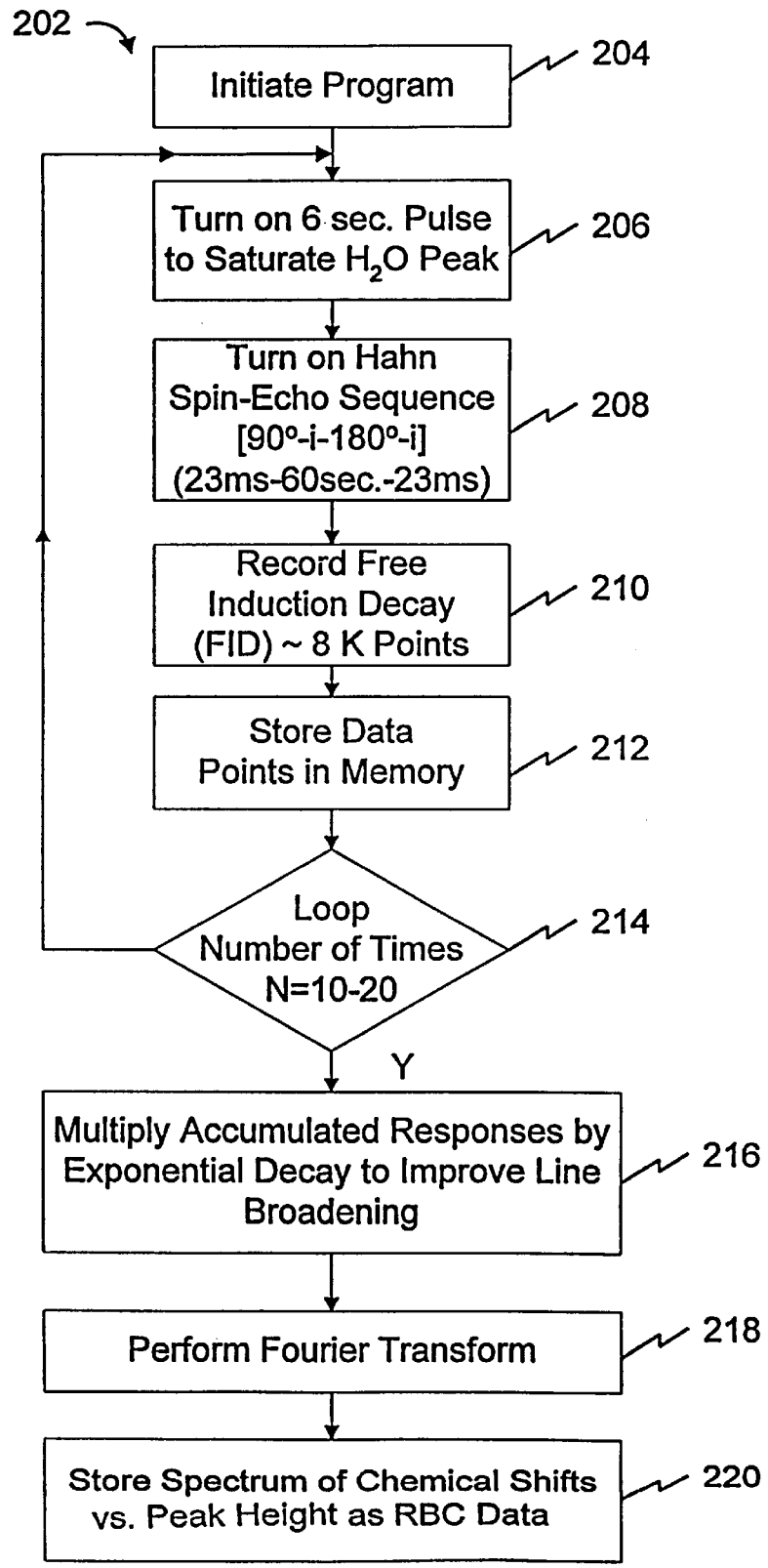
FIG. 4 is a flow chart depicting an in vitro $^1$H MRS reading cycle employed to analyze an ethanol-treated erythrocyte sample.

Briefly, the method of MRS spectrum analysis typically employs the following well-known steps. The following discussion makes reference to the flowchart 202 in FIG. 4. A biasing magnetic field is applied to a sample, this sample in the present invention being either ethanol-treated blood plasma or erythrocytes, step 204. The biasing magnetic field is sufficient to align at least the protons in the sample to an initial orientation. Thereafter, a resonating magnetic field is applied to said sample to flip the protons between a further position and the initial position, step 208. The spectrometer senses, as analog signals, magnetic changes as the bonds flip from the further position back to the initial position, step 210. The analog signals are thereafter converted into digital signals and then stored as patient data in a memory, step 212. Typically, ten or more scans are performed to obtain a plurality of separate digital signals, step 214. The accumulated digital signals are recalled from memory and are multiplied by an exponential decay to improve line broadening, step 216. The multiplied data is thereafter transformed with a Fourier transform equation, step 218. A spectrum of chemical shift versus peak height is constructed from the accumulated data.

Typically, the steps in the previous paragraph are repeated for one or more standard samples that include erythrocytes from subject(s) having a predetermined and documented past history of alcohol self-administration, i.e. known alcohol tolerant individuals and known alcohol non-tolerant individuals. A spectrum of chemical shifts versus peak height for the first standard sample is compared is constructed from the accumulated data.

The proton or $^1H$ nucleus is an excellent NMR probe because it is present in nearly all organic compounds and affords relatively good sensitivity. Presaturation is typically employed to suppress the extremely intense water peaks, step 206. The use of high frequency (greater than or equal to 300 MHz) and presaturation allows NMR to be an effective tool for analyzing biological specimens, such as the erythrocytes and plasma analyzed herein. Standards and unknowns are examined under identical instrumental conditions. Spin-echo NMR is employed to measure the alcohol concentration in erythrocytes since conventional high-resolution spectra are obscured by broad hemoglobin resonances, step 208. (Jones, A. J. et al., "Measurement of choline concentration and transport in human erythrocytes by $^1H$ NMR: Comparison of normal blood and that from lithium treated psychiatric patients," *Clin. Chim. Acta* 104:77–85 (1980) and Brown, F. F. et al., "Human erythrocyte metabolism studies by $^1H$ spin echo NMR," *FABS Lett.* 82:12–16 (1977)). Serum concentrations can be measured by the methods described herein or alternatively by methods described by Bach, J. L., "Analysis of serum by high-yield proton nuclear magnetic resonance," *Clin. Chem.* 28: 1873–1877 (1982).

Preferred parameters for MRS measurement of the erythrocyte are as follows:

NMR spectroscopy can be performed on a high frequency spectrometer, for example, 300 or 500 MHz frequencies. Spectra are obtained in the Fourier transform mode using quadrature detection. The spectral width is preferably 5000 Hz. From 4K to 16K data points can be used. 8K data points provide acceptable results. The water resonance is irradiated to achieve pre-saturation. Irradiation should occur for about 1 to about 10 seconds, preferably 6 seconds. A Hahn spin-echo sequence is employed for acquisition [90°-τ-180°-τ- acquisition] (Rabenstein et al., *J. Biochem. Biophys.* 9:277–306 (1984)). Lorentzian line broadening is preferably applied before Fourier transformation. Typically, 10–20 averages are acquired for each spectrum, although the number of acquisitions can vary greatly, for instance, from about 5 to about 100. These parameters can be varied by the artisan of ordinary skill so long as the ethanol peak and a concentration standard peak are acquired with sufficient resolution to allow for the determination of the areas under each peak.

The preferred method for determining plasma ethanol concentration is by the same in vitro MRS technique employed to determine the measurable erythrocyte ethanol concentration. Other techniques may be employed, so long as the same technique is consistently employed to measure both the subject's plasma ethanol concentration and to measure the plasma ethanol concentrations for one or more standards as described above. For instance, plasma ethanol concentrations can also be measured in duplicate using a sensitive and well-validated gas chromatographic method. See, Gentry et al., *Physiology and Behavior* 31: 529–532 (1983) who modified a procedure described earlier by Freund (Freund, *Analytical Chemistry.* 39:545–546 (1967)). Analysis is carried out using a Hewlett-Packard mode 5890 Gas Chromatograph, equipped with an automatic liquid sample injector, a mode 3393A Integrator/Recorder, a six-foot coiled glass column (2 mm inner diameter, ¼ inch outer diameter) packed with Chromosorb 101, 80/100 mesh; the carrier gas is nitrogen, column oven temperature is 130° C., and the injection port temperature is 175° C.

The following example is illustrative, but not limiting, of the method of the present invention. Other suitable modifications and adaptations of the variety of conditions and parameters normally encountered in clinical diagnoses and obvious to those skilled in the art are within the spirit and scope of the invention.

EXAMPLE 1

In vitro Detection of Ethanol in Human Erythrocytes and Plasma by MRS

Venous blood samples were obtained from voluntary, healthy subjects and were collected in vacutainer tubes (Becton Dickinson, N.J., USA) containing EDTA (ethylenediamine tetraacetic acid) as anticoagulant. The samples were separated into red blood cells and plasma by centrifugation (3440 g, 3 min). Ethanol (40%, vodka), diluted with saline solution, was added to the red blood cell fraction and to the plasma fraction so that the final ethanol concentration in each was 100 mg/dl (21.7 mM). Oxygen was bubbled through the red blood cell fraction for about 2 minutes to ensure that the hemoglobin was in the diamagnetic oxygenated form. These samples were then introduced into 5 mm O.D. NMR tubes (Wilmad Glass Co., New Jersey, USA). The effective volume of the red blood cells available for signal sampling was about 0.2 cc.

Sodium formate (0.216M) dissolved in $D_2O$ in a coaxial capillary (Wilmad Glass Co., New Jersey, USA) was used as the concentration standard.

NMR spectroscopy was formed using a General Electric GN 300 spectrometer operating at 300 MHz. Spectra were obtained in the Fourier transform mode using quadrature detection. The spectral width was 5000 Hz and 8K data points were used. Spectra were acquired with the water resonance being irradiated for 6 sec to achieve pre-saturation, followed by a Hahn spin-echo sequence [90°-τ-180°-τ-acquisition] (Rabenstein et al., 1984). Irradiation (τ) is set to ½ J, where J=7 Hz for the triplet (methyl protons) of the ethanol resonance. The CW irradiation was gated on during τ to minimize $T_1$ recovery of the water resonance. The 90° pulse duration was 23 μs, and the interpulse delay was 60 sec. Lorentzian line broadening of 1.0 Hz was applied before Fourier transformation. Typically, 10–20 averages were acquired for each spectrum, although the number of acquisitions can vary greatly.

Figure 1A:
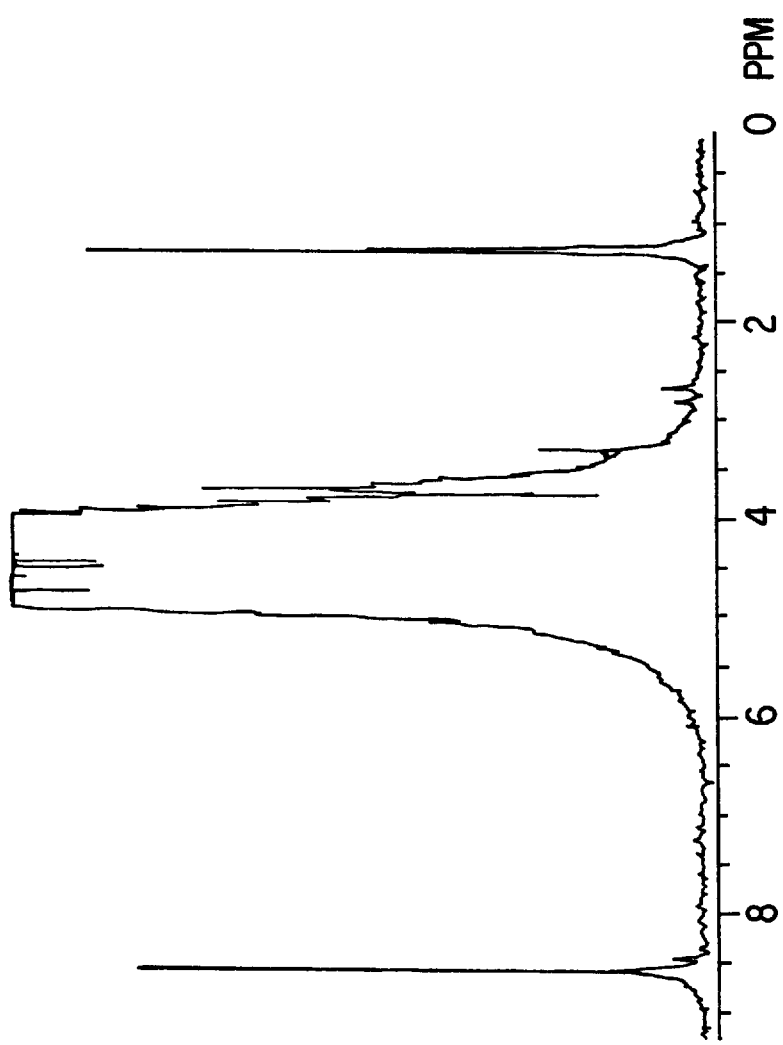
FIG. 1A is a representative 300 MHZ $^1$H MRS spectrum of human plasma containing EDTA and 100 mg/dl (21.7 mM) ethanol.
Figure 1B:
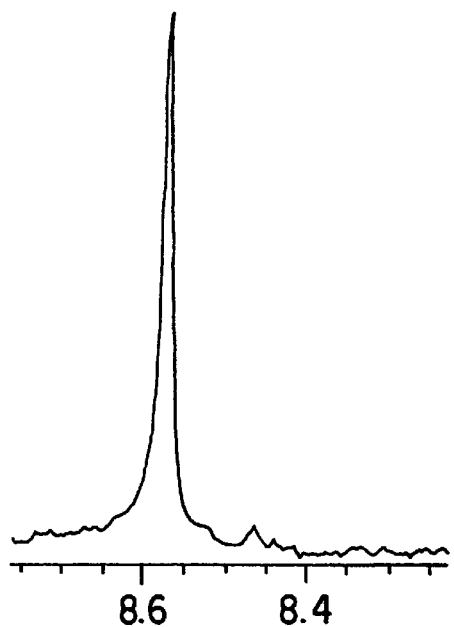
FIG. 1B is an expanded offset of the spectrum shown in FIG. 1A.
Figure 1C:
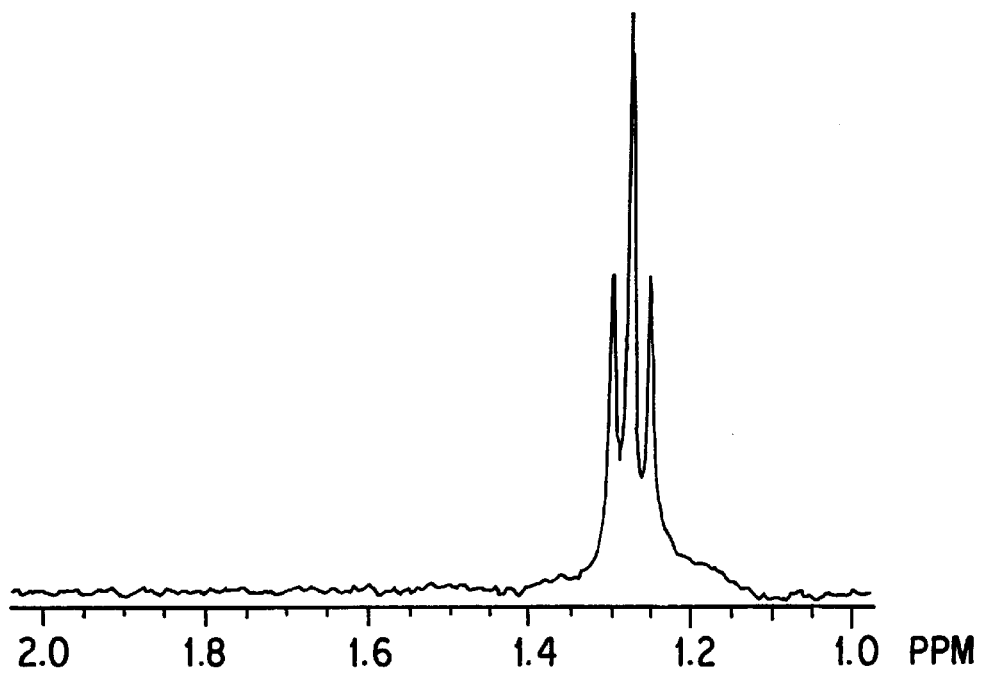
Figure 2A:
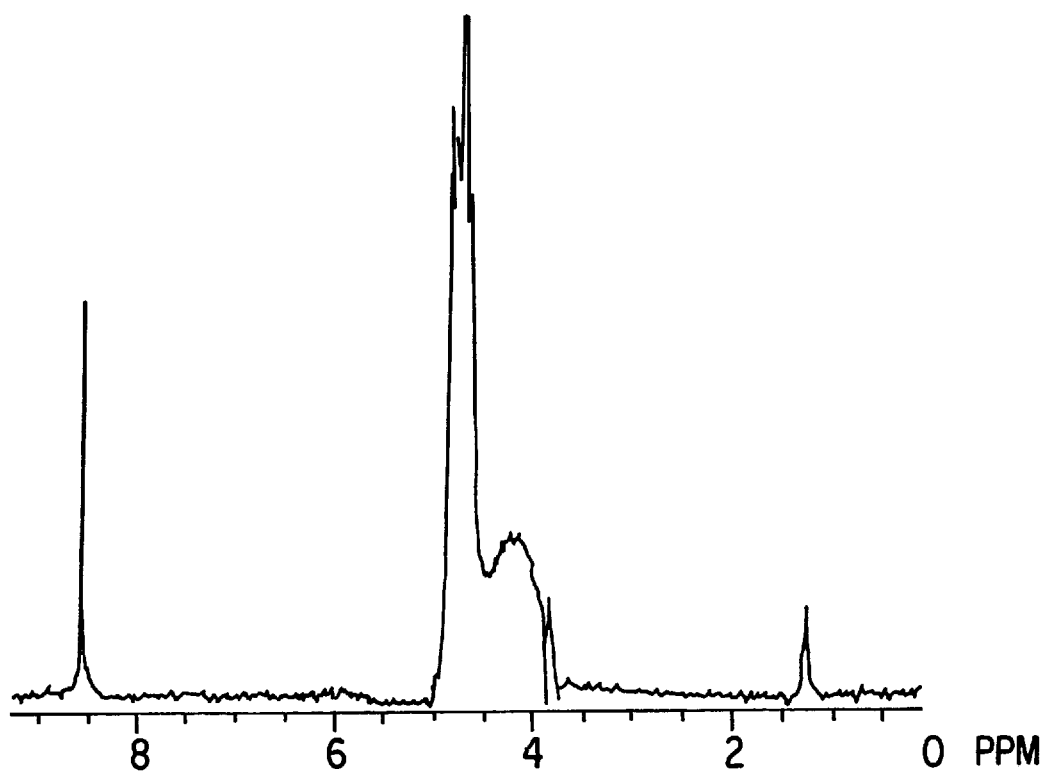
FIG. 2A is a representative 300 MHZ $^1$H MRS spectrum of human erythrocytes taken from a non-tolerant human subject in a solution containing EDTA and 100 mg/dl (21.7 mM) ethanol.
Figure 2B:
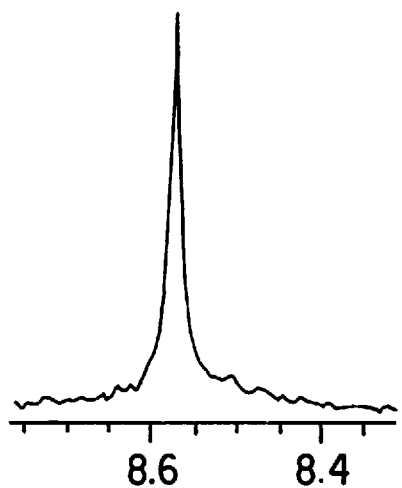
FIG. 2B is an expanded offset of the spectrum shown in FIG. 2A.
Figure 2C:
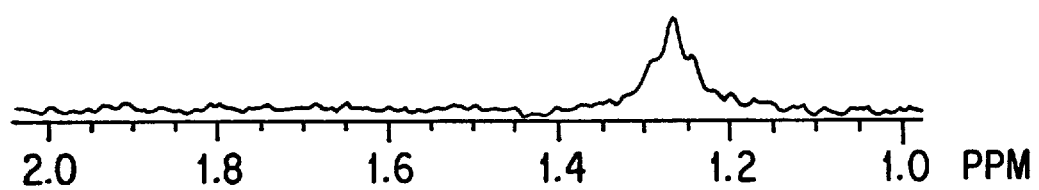

The results (FIG. 1A and FIG. 1B) show essentially complete detection of ethanol in human plasma samples (~99%). As in previous in vivo magnetic resonance spectroscopy (MRS) studies of brain ethanol in humans, $^1H$ NMR recovers about ~30% of ethanol in red blood cells of healthy non-tolerant drinkers in vitro (FIG. 2A and FIG. 2B). Although fewer membranous structures are present in red blood cells than in neurons similar mechanisms (hydrogen bonding of ethanol molecules to the membrane phospholipid head groups and solubilization of ethanol within bilipid membrane layers) that were postulated for partial ethanol detectability in neurons are believed to be operative in the red blood cells.

The results show that erythrocyte ethanol detection by in vitro proton magnetic resonance spectroscopy in alcohol-tolerant drinkers parallels brain ethanol detection by in vivo proton MRS. Therefore, the MRS-measured erythrocyte alcohol concentration will be significantly greater in tolerant individuals compared to their non-tolerant counterparts when erythrocyte preparations of each are mixed with equal amounts of ethanol. MRS evaluation of erythrocyte ethanol concentrations, may facilitate a better understanding of the basic biological processes of alcohol tolerance and also contribute to improved clinical diagnosis and treatment of alcoholism.

EXAMPLE 2

Generation of Alcohol Tolerant and Non-Tolerant Standard Ratios

This example is directed towards the generation and analysis of $[EtOH]_{RBC/MRS}:[EtOH]_{PLASMA}$ ratios for a group of known alcohol tolerant individuals and a group of alcohol non-tolerant individuals. Venous blood samples are obtained voluntarily from eight healthy adult males after an overnight fast (10 hours) and are collected in vacutainer tubes (Becton Dickinson, N.J., USA) containing EDTA (ethylenediamine tetraacetic acid) as anticoagulant. The occasional drinkers are four men (age range 20–35 years) who consume 24 drinks/week. These men are designated as non-tolerant alcohol consumers. The heavy drinkers are four men (age range 20–35 years) who regularly consume 10–20 drinks/week. These men are designated as acquired alcohol-tolerant individuals. There are no statistically significant differences between the tolerant and non-tolerant groups with respect to age, height, weight, socioeconomic status, years of education, or other significant demographic variables. No subject has any Axis I or Axis II psychiatric diagnosis based upon DSM III-R criteria. No subject has any past history of alcohol or drug abuse or dependence, and none has any family history of alcoholism. All subjects have normal physical examinations, blood chemistry, and blood hemogram studies. Urine drug screens are negative for all subjects.

The blood samples are separated, treated with ethanol and analyzed by proton MRS according to the procedure given in Example 1.

The average erythrocyte to plasma ethanol ratio is calculated for each subject. For non-tolerant subjects, calculated mean erythrocyte ethanol concentration is approximately 30% of the measured plasma ethanol levels. The erythrocyte to plasma ratios for tolerant subjects are significantly greater than for non-tolerant subjects.

Having now fully described this invention, it will be understood by those of ordinary skill in the art that the same can be performed within a wide and equivalent range of conditions, scanning parameters, data acquisition parameters, concentration calculation algorithms and other parameters without affecting the scope of the invention or any embodiment thereof. All patents and publications cited herein are fully incorporated by reference herein in their entirety.

What is claimed is:

1. A method of determining the history of frequency and amount of alcohol self-administration by a subject, comprising the steps of:

(a) obtaining a blood sample from a subject;

(b) separating the sample into a plasma fraction and an erythrocyte fraction;

(c) adding an equivalent amount of an ethanol solution to each of said fractions to form an ethanol/erythrocyte solution and an ethanol/plasma solution;

(d) bubbling oxygen through the ethanol/erythrocyte solution to form an oxygenated ethanol/erythrocyte solution;

(e) acquiring one or more proton magnetic resonance spectra of the oxygenated ethanol/erythrocyte solution;

(f) obtaining the MRS-measured erythrocyte ethanol concentration ($[ETOH]_{RBC/MRS}$) from said one or more spectra;

(g) obtaining the ethanol concentration of the ethanol/plasma solution (h) calculating the ratio of MRS—measured erythrocyte ethanol concentration to plasma ethanol concentration to obtain a test ratio ($\{[ETOH]_{RBC/MRS}:[ETOH] PLASMA\}_{TEST}$); and (I) comparing said test ratio to one or more known standard values for control subjects having a known past history of frequency and amount of alcohol self-administration;

whereby the subject's past history of frequency and amount of alcohol self-administration is classified according to the test ratio's relationship to said standard values.

2. The method of claim 1, wherein the blood sample is a venous blood sample.

3. The method of claim 1, wherein the blood sample is separated into plasma fraction and an erythrocyte fraction by centrifugation.

4. The method of claim 1, wherein the standard value is obtained by analysis of blood samples taken from one or more individuals who do not self-administer alcohol.

5. The method of claim 1, wherein the ethanol solution in step (c) is a solution comprising ethanol and saline solution, and is added to each fraction until a final ethanol concentration of 100 mg/dL is reached.

6. A method of monitoring the adequacy or duration of alcohol abstinence in a subject comprising the steps of:

(a) obtain a blood sample from a test subject;

(b) separate the sample into an erythrocyte fraction and a plasma fraction;

(c) incubate each fraction with a fixed amount of ethanol;

(d) oxygenate the ethanol-treated erythrocyte fraction;

(e) determine ethanol concentration of the oxygenated, ethanol-treated erythrocyte fraction by MRS ($[EtOH]_{RBC/MRS}$);

(f) determine ethanol concentration of the ethanol-treated plasma fraction ($[EtOH]_{PLASMA}$);

(g) obtain a test ratio of $[ETOH]_{RBC/MRS}:[EtOH]_{PLASMA}$; and (h) compare the test ratio to a known standard value for one or more control subjects having a known past history of alcohol abstinence, whereby the test subject's abstinence can be determined by a progressively decreasing test ratio that approaches the standard value.

7. The method of claim 6, wherein said subject is a recovering alcoholic.

8. The method of claim 6, wherein the blood sample is a venous blood sample.

9. The method of claim 6, wherein the blood sample is separated into plasma fraction and an erythrocyte fraction by centrifugation.

10. The method of claim 6, wherein the standard value is obtained by analysis of blood samples taken from one or more individuals who do not self-administer alcohol.

11. The method of claim 6, wherein the ethanol solution in step (c) is a solution comprising ethanol and saline solution, and is added to each fraction until a final ethanol concentration of 100 mg/dL is reached.

12. A method for determining whether a subject is alcohol tolerant or non-tolerant, comprising the following steps:

(a) obtain a blood sample from a test subject;

(b) separate the sample into an erythrocyte fraction and a plasma fraction;

(c) incubate each fraction with a fixed amount of ethanol;

(d) oxygenate the ethanol-treated erythrocyte fraction;

(e) determine ethanol concentration of the oxygenated, ethanol-treated erythrocyte fraction by MRS ($[EtOH]_{RBC/MRS}$);

(f) determine ethanol concentration of the ethanol-treated plasma fraction ($[EtOH]_{PLASMA}$);

(g) obtain a test ratio of $[EtOH]_{RBC/MRS}:[EtOH]_{PLASMA}$; and (h) compare the test ratio to a known standard value obtained from one or more control subjects that are known to be either alcohol tolerant or alcohol non-tolerant, whereby a test ratio which is elevated compared to said standard value obtained from one or more alcohol non-tolerant control subjects is indicative that the subject is alcohol tolerant.

13. The method of claim 12, wherein the blood sample is a venous blood sample.

14. The method of claim 12, wherein the blood sample is separated into plasma fraction and an erythrocyte fraction by centrifugation.

15. The method of claim 12, wherein the standard value is obtained by analysis of blood samples taken from one or more individuals who do not self-administer alcohol.

16. The method of claim 12, wherein the ethanol solution in step (c) is a solution comprising ethanol and saline solution, and is added to each fraction until a final ethanol concentration of 100 mg/dL is reached.

* * * * *